(12) United States Patent
Agreli et al.

(10) Patent No.: US 12,582,748 B2
(45) Date of Patent: Mar. 24, 2026

(54) SELF-EXTENDABLE STENT FOR PULMONARY ARTERY

(71) Applicant: P+F Products + Features GmbH, Vienna (AT)

(72) Inventors: Guilherme Agreli, Sao Jose de Rio Preto (BR); Katharina Kiss, Vienna (AT); Siegfried Einhellig, Vienna (AT)

(73) Assignee: P+F Products + Features GmbH, Vienna (AT)

( * ) Notice: Subject to any disclaimer, the term of this patent is extended or adjusted under 35 U.S.C. 154(b) by 896 days.

(21) Appl. No.: 17/669,644

(22) Filed: Feb. 11, 2022

(65) Prior Publication Data

US 2022/0257835 A1     Aug. 18, 2022

(30) Foreign Application Priority Data

Feb. 18, 2021    (EP) ..................................... 21157895

(51) Int. Cl.
| | |
|---|---|
| *A61F 2/24* | (2006.01) |
| *A61L 27/18* | (2006.01) |
| *A61L 27/36* | (2006.01) |

(52) U.S. Cl.
CPC ........ *A61L 27/3625* (2013.01); *A61F 2/2418* (2013.01); *A61F 2/243* (2013.01);
(Continued)

(58) Field of Classification Search
CPC ..... A61L 27/3625; A61F 2/2418; A61F 2/243
See application file for complete search history.

(56) References Cited

U.S. PATENT DOCUMENTS

| | | | | |
|---|---|---|---|---|
| 3,671,522 A | * | 6/1972 | Hagen | ....................... C14C 9/00 |
| | | | | 544/335 |
| 5,368,608 A | * | 11/1994 | Levy | ....................... A61L 27/54 |
| | | | | 8/94.28 |

(Continued)

FOREIGN PATENT DOCUMENTS

| | | |
|---|---|---|
| EP | 3693030 A1 | 8/2020 |
| EP | 3744291 A1 | 12/2020 |

*Primary Examiner* — Suzette J Gherbi
(74) *Attorney, Agent, or Firm* — Vivacqua Crane, PLLC

(57) ABSTRACT

The invention relates to a self-expandable stent, especially a pulmonary stent, with a proximal section, a middle section and a distal section arranged at a longitudinal axis of the stent, the stent having a dry valve made of bovine pericardium arranged at the middle section thereof, a skirt surrounding the dry valve at least at the middle section and made of one of bovine pericardium and polyester, wherein the stent further comprises eyelets arranged at a distal end at the distal section and/or a proximal end at the proximal section for fixing the stent at an artery, and wherein the stent comprises a frame composed of a plurality of arms forming the proximal, the middle and the distal section with the sections being interconnected, and the stent comprising a fixture area at the middle section of the frame with the arms being arranged in parallel to each other at the fixture area and the middle section comprising one or more fixture openings at said fixture area for fixing the valve at the frame. The invention further relates to A delivery device for delivering a self-expandable stent according to claims 1 to 14, the delivery device comprising a flush port, a main body part for holding, inflating and/or releasing the stent, and an actuation mechanism for moving the stent to a delivery site, and/or wherein the actuation mechanism has a torque control and can rotate the stent about an axis of the main body, and/or the delivery device having a knob or the like at the actuation
(Continued)

mechanism, with the knob in particular being able to be rotated about an axis of rotation of the actuation mechanism.

22 Claims, 5 Drawing Sheets
(4 of 5 Drawing Sheet(s) Filed in Color)

(52) U.S. Cl.
CPC ........... *A61L 27/18* (2013.01); *A61L 27/3687* (2013.01); *A61L 2430/20* (2013.01)

(56) References Cited

U.S. PATENT DOCUMENTS

| | | | | |
|---|---|---|---|---|
| 8,357,387 B2 * | 1/2013 | Dove | ................. | A61L 27/3629 |
| | | | | 424/423 |
| 8,748,490 B2 * | 6/2014 | Dove | .................... | A61F 2/2415 |
| | | | | 514/557 |
| 2005/0137701 A1 * | 6/2005 | Salahieh | ............... | A61F 2/2412 |
| | | | | 623/1.36 |
| 2008/0154358 A1 * | 6/2008 | Tansley | .................. | A61F 2/2415 |
| | | | | 623/2.14 |
| 2009/0164005 A1 * | 6/2009 | Dove | .................... | A61F 2/2412 |
| | | | | 435/1.1 |
| 2009/0254175 A1 * | 10/2009 | Quijano | ................ | A61F 2/2475 |
| | | | | 623/1.24 |
| 2009/0287299 A1 * | 11/2009 | Tabor | ....................... | A61F 2/013 |
| | | | | 623/1.26 |
| 2011/0214398 A1 * | 9/2011 | Liburd | ................... | B65D 77/20 |
| | | | | 53/467 |
| 2011/0301700 A1 | 12/2011 | Fish et al. | | |
| 2014/0277390 A1 * | 9/2014 | Ratz | ..................... | A61F 2/2418 |
| | | | | 623/1.26 |
| 2021/0187135 A1 * | 6/2021 | Claessens | ............. | A61F 2/0095 |
| 2022/0151775 A1 * | 5/2022 | Kiss | ....................... | A61F 2/2418 |
| 2022/0257374 A1 * | 8/2022 | Agreli | ................... | A61F 2/2418 |
| 2022/0257834 A1 * | 8/2022 | Agreli | ................ | A61L 27/3641 |

* cited by examiner

SELF-EXTENDABLE STENT FOR PULMONARY ARTERY

CROSS REFERENCE TO RELATED APPLICATIONS

This application claims the benefit of foreign priority under 35 U.S.C, § 119 of European patent application number 21157895.0, filed Feb. 18, 2021. The contents of this application are incorporated herein by reference in their entirety.

INTRODUCTION

The invention relates to a self-extendable stent, especially a pulmonary stent and a delivery device for delivering a self-expandable stent.

A healthy heart function provides necessary blood flow to the body. The anatomy of the heart is comprised of four chambers: the right atrium, right ventricle, left atrium and left ventricle. There are valves located between the two right chambers (tricuspid valve) and the left chambers (mitral valve), Blood travels from the caval veins, the superior vena cava and inferior vena cava,to the right atrium. From the right atrium, blood passes through the tricuspid valve into the right ventricle. From there, blood flows through the pulmonary valve to the lungs. Following oxygenation, the blood flows back to the left atrium, through the mitral valve and into the left ventricle, Blood is then pushed through the aortic valve and from there, ultimately, to the rest of the body.

The pulmonary valve is the semilunar valve of the heart that is located between the right ventricle and the pulmonary artery. The pulmonary valve comprises three cusps (leaflets). The base of these leaflets is attacked to the opening connecting the pulmonary artery and the ventricle, i. a the truncus pulmonalis. Similar to the aortic valve, the pulmonary valve opens in ventricular systole, when the pressure in the right ventricle rises above the pressure in the pulmonary artery. At the end of the ventricular systole, when the pressure in the right ventricle falls rapidly, the pressure in the pulmonary artery causes the pulmonary valve to close such that it prevents a backflow of blood at the beginning of the relaxation phase (diastole) of the heart.

Pulmonary valve disease is a condition in which the pulmonary valve doesn't work properly. The condition can interrupt blood flow from the heart to the lung. It may occur on its own or as part of other congenital heart defects, such as tetralogy of Fallot. Often, the condition may only be detected by a physical evaluation or heart imaging for another reason.

The case where the pulmonary valve no longer closes properly is called a pulmonary valve insufficiency. Insufficient opening, on the other hand, is called a pulmonary stenosis. Both functional disorders require the heart to work harder to pump and thus overload the heart muscle.

Types of pulmonary valve disease that may require treatment with pulmonary valve repair or pulmonary valve replacement include pulmonary valve regurgitation, pulmonary valve stenosis and pulmonary atresia.

A leaky pulmonary valve allows blood to flow backward into the heart (pulmonary valve regurgitation) rather than directly to the lungs for oxygen. In the second condition, i. e, the pulmonary valve stenosis, the pulmonary valve is thickened or obstructed, which makes it harder for it to open properly. As a result, the heart has to work harder to pump blood into the pulmonary artery and to the lungs. The pulmonary valve atresia relates to a congenital heart defect in which a child is born without a well-defined pulmonary valve. In pulmonary atresia, blood cannot flow from the right ventricle into the pulmonary artery. The only blood flow to the lungs is through an open passageway between the pulmonary artery and the main artery supplying blood to the body (aorta).

Pulmonary valve repair or pulmonary valve replacement can treat the above pulmonary valve diseases and help restore normal blood flow, reduce symptoms, prolong life and help preserve the function of your heart muscle. In general, the decision to repair or replace a damaged pulmonary valve depends on many factors such as the severity of the disease, the age and overall health of the patient or maybe even whether a patient needs a heart surgery to correct another heart problem in addition to the pulmonary valve disease such that both conditions can be treated within one surgery.

Up to date, pulmonary valve repair is the preferred option because it's associated with a lower risk of infection, preserves valve strength and function, and eliminates the need to take blood-thinning medications, which may be necessary with pulmonary valve replacement.

Pulmonary valve repair and pulmonary valve replacement surgery risks vary depending on the health of the patient, the type of procedure and the expertise of the surgeon and health care team. Risks associated with pulmonary valve repair and pulmonary valve replacement, i, a with open heart surgeries in general, may include bleeding, blood clots, heart rhythm problems, infections, heart attacks, strokes or even death. Another risk arises in connection with the artificial replacement valves which may show a disfunction.

Therefore, biological tissues are widely used to make prosthetic replacements for heart valves and blood vessels as well as for transcatheter heart valves. They are connective tissues comprising collagen as the main component. Among these tissues, bovine pericardium is one of the most widely employed. Pericardial tissue is the sac surrounding the heart which provides a natural barrier to infection for the heart and prevents adhesion to the surrounding tissue. The pericardium also serves mechanical roles, for example, by preventing over dilation of the heart, maintaining the correct anatomical position of the heart, and regulating the pressure to volume ratio in the left ventricle during diastole. The structure of the tissue determines its behaviour under loading in both conditions physiologic to the pericardium and as a prosthetic device.

However, biological tissues obtained from the abattoir, in particular porcine and bovine cadavers, begin to degrade immediately. Therefore, the storage of such materials has proven to be difficult. For this purpose, a biological tissue, such as e.g. bovine or porcine pericardium or a heart valve, is usually chemically treated to improve its mechanical performance and immunogenic properties, reduce thrombogenicity and degradation, preserve sterility, and prolong the allowable storage period.

Accordingly, biological tissues are known which can be used as bioprosthetic devices that can be stored dry before used for clinical applications. Additionally, special care has to be taken in connection with the preparation methods in order to avoid the formation of degenerative calcific deposits. Calcification, in particular pathologic calcification, of soft biological tissues due to deposition of calcium phosphate mineral salts in an implanted tissue is undesirable and the deposition of the calcific deposits can have severe consequences on device performance. Calcification of implants can lead to stiffening, structural instability and ultimately to device failure.

Although there are difficulties in the usage of biological tissues, their performance inside a human body has proven to be significantly better.

SUMMARY

It is therefore an object of the invention to provide a self-extendable stent and a delivery device for a self-expandable stent with which the above mentioned drawbacks can be overcome. This object is solved by the subject matter of the independent claims.

In particular, in a first aspect the invention provides a self-expandable stent, especially a pulmonary stent, with a proximal section, a middle section and a distal section arranged at a longitudinal axis of the stent, the stent having a dry valve made of bovine pericardium arranged at the middle section thereof, a skirt surrounding the dry valve at least at the middle section and made of at least one of bovine pericardium and polyester. The stent further comprises eyelets arranged at a distal end at the distal section and/or a proximal end at the proximal section for fixing the stent at an artery, especially the pulmonary artery of a patient. Additionally, the stent comprises a frame composed of a plurality of arms forming the proximal, the middle and the distal section with the sections being interconnected, and a fixture area at the middle section of the frame with the arms being arranged in parallel to each other at the fixture area. The middle section further comprises one or more fixture openings at said fixture area for fixing the valve at the frame.

Thus, the present disclosure relates to the invention of a medical device for minimally invasive of a pulmonary valve condition. In this connection it is noted that the expressions "proximal" and "distal" relate to the position of the stent in use, i.e. to positions closer to and further away from the heart.

The invention provides a stent with a proximal section, a middle section and a distal section arranged at a longitudinal axis of the stent, which can be fixed at a point of interest such as the pulmonary artery in order to treat one of the above mentioned diseases. In order to seal the fixing point, the stent further comprises a skirt, which is surrounds the dry valve at least at the middle section. The skirt therefore provides sealing between the stent and the right ventricle of the heart. Said skirt is made of one of bovine pericardium and polyester.

To assist the fixation of the valve to the heart the valve may have a PET fabric skirt that attaches the tissue to the stent frame, PET material is highly inert and does not create any adverse reaction in human body. The PET material also permits ingrowth of cells into the cloth which helps hold the valve in place minimizing thrombosis at the same time.

Generally speaking PTFE suture lines may be used for fixation on fixing the stent to the heart.

Additionally, the stent further comprises eyelets arranged at a distal end at the distal section and/or a proximal end at the proximal section for fixing the stent at an artery, i. a the pulmonary artery of a patient, or at the transition between the pulmonary artery and the right ventricle of the heart such that it can be ensured that the stent remains at its intended place.

The stent further comprises a dry valve made of bovine pericardium, which upon final placement at the point of interest can be rehydrated with a solution such as a saline solution. Hence, a pericardium as an animal biological tissue material is used, in particular obtained from a bovine heart that may have been treated with a crosslinking agent. The natural human heart valve, which is supposed to be fixed with the invention, is identified as the pulmonary valve. Therefore, the pericardium is used to replace the damaged or diseased naturally occurring heart valve. Also, such a valve can allow the pre-loading of the stent within a delivery system.

The valves are thus made using bovine pericardium. The ECM (Extracellular Matrix) tissue is generally harvested from the pericardial sac of cows and is then used to manufacture the leaflets. The tissue from pericardial sac is particularly well suited for a valve leaflet due to its durable physical properties. The tissues are glutaraldehyde fixed, non-viable, chemically treated (decellularized) and sterilized so that the biological markers are removed making them more compatible with the patient's immune system.

Preferably, there are three leaflets used for the valve included in the stent that can be fixed to the pulmonary artery.

The potential benefits of bovine pericardium are superior biocompatibility, demonstrates minimal suture line bleeding and patency can be immediately confirmed by ultrasound, such as TEE ultrasound. They also have benefits like lack of calcification, support of cellular ingrowth and reduced rates of restenosis and infection. The pericardium is durable, strong and available in various sizes.

Furthermore, the stent comprises a plurality of arms which build the frame of the stent, i, e. the three interconnected parts (proximal, middle and distal section). The expansion of the stent is made possible by the plurality of arms that are interconnected in such a way that following the expansion they adapt to the anatomical need of the location of the stent. In this way the design of such a stent is adapted to accommodate the anatomical needs and implantation locations. The stent furthermore consists of a self-expandable stent frame. Moreover, between 6 and 50 arms can be provided to form the stent frame.

Moreover, said frame can be composed of Nitinol. Nitinol is a collapsible and flexible metal, which is furthermore self-expandable and comprises a shape-memory. Hence, the frame can automatically self-expand to an outer shape, which can be chosen beforehand since the Nitinol can memorize said chosen shape.

In order to fix the dry valve to the frame, the stent comprises a fixture area at the middle section of the frame where the arms are arranged in parallel to each other at the fixture area and where the frame comprises or more fixture openings for suturing the valve to the frame. In this connection it is noted that said fixture openings can either be present in the arms or respectively between the arms which are directly connected to on another, Furthermore, it may not be necessary to attach the valve at each arm of the frame.

The exact amount of attachment points, i. e. fixture openings, may be chosen as needed.

According an embodiment of the invention the middle section comprises a length which is approximately 5 to 30% of a total length of the stent. Hence, the middle section may comprise a length that corresponds to a length of the fixture area or may comprise a length that is greater than the length of the fixture area.

Also, as already mentioned above, the stent can be divided into three parts, wherein the middle section is arranged between the proximal and the distal section. The lengths, sizes and dimensions of the respective parts are believed to be particularly suitable for a minimally invasive treatment of pulmonary artery diseases. Selecting the length of the middle section to be longer than that of the proximal or distal section may enable an interference fit between the stent and the pulmonary artery to be sufficient to prevent the stent from becoming dislodged in time.

According to another embodiment one or more, preferably two or more, especially three such openings are provided in one or more arms of the middle section, i. a in the fixture area. The exact amount of fixture openings may vary with the biological tissue being used or with the exact size of the stent. Either way, the amount of fixture openings can be chosen accordingly.

The dry bovine pericardium may have a maximum tensile stress selected in the range of 20 to 25 MPa, and/or wherein the rehydrated bovine pericardium has a tensile stress selected in the range of 12 to 15 MPa, Thus, the dry bovine pericardium can comprise a tensile resistance which can be up to 15 times higher than the tensile resistance of the leaflets of a human heart. This is mainly done for safety reasons in order to minimize tearing or fracture of the pericardium.

The mechanical properties of a material, in particular tensile strength, can be tested under strain-stress evaluation using Universal Testing Machine (Oswaldo F lizzola, model AME-2kN).

Furthermore, the dry bovine pericardium may have a calcium content selected in the range of 0.01 to 0.1 g/Kg. The bovine leaflets may generally be as flexible and durable similar to the patient's natural tissue and therefor individual with such replacement valve may not require blood thinner medication on a continuous basis. Bovine pericardium tissue provide better hemodyn mics in view of their similarity to natural flexible leaflet valves, some bovine pericardium valves may have some limitation on durability due to calcification and degeneration process. Treating the valves with a specialized anti-calcification treatment makes them more resistant to calcification. The valves having such a calcium content are hence more resistant to calcification and are more durable wherein the dry valve comprises between two and six leaflets, preferably three or four leaflets. It has shown that for stents shaped circularly in the region of attachment of the valve, a valve comprising three leaflets is the best option in order to distribute the forces of the blood flow present in the heart evenly during the opening and closing process of the valve.

According to another embodiment of the invention the dry bovine pericardium is formed by treating using a method comprising the following steps:

(1) soaking of the bovine pericardium treated with a crosslinking agent with a saline solution;

(2) contacting the soaked bovine pericardium with an aqueous solution comprising Hydrogen Peroxide;

(3) contacting the bovine pericardium with an aqueous solution comprising PBS and EDTA;

(4) contacting the bovine pericardium with a solution comprising glycerol, ethanol and EDTA; and (5) contacting the bovine pericardium with a glycerol solution.

One embodiment of the present invention utilizes soaking of the bovine pericardium treated with a crosslinking agent with a saline solution, As used herein, a crosslinking agent is glutaraldehyde which is preferably used in biochemical and medicine applications as an amine-reactive homobifunctional cross-linker. As already mentioned above, glutaraldehyde treatment produces stable cross-links in cellular and extra-cellular matrix proteins which substantially reduced graft immunogenicity. However, such tissue has altered mechanical property, early mechanical failure, cytotoxicity, and incomplete suppression of immunological recognition. Besides this severe calcification was noticed in glutaraldehyde-treated bovine pericardium. An emerging alternative to glutaraldehyde treatment is further treatment according to the method steps, i.e. a method allowing to reduce calcification of the bovine pericardium.

It is preferably to use the crosslinking agent in an amount of from 0.1% to 5.0% by volume, more preferably from 0.2% to 3.0% by volume, further preferably from 0.3% to 2.0% by volume and especially preferably from 0.5% to 1.0% by volume.

In this respect, as a first step a soaking of the bovine pericardium with an aqueous saline solution comprising 0.9% of sodium chloride (9.0 g per litre) is carried out. Such a solution is also commonly named as normal saline, physiological saline or isotonic saline solution.

In a second step, the soaked bovine pericardium is contacted with an aqueous solution comprising Hydrogen Peroxide. It is preferred that the concentration of hydrogen peroxide is from 0.05% by volume to 5.0% by volume, preferably from 0.1% by volume to 3.0% by volume, more preferably from 0.2% by volume to 2.0% by volume.

In a third step of the present invention, the bovine pericardium is contacted with an aqueous solution comprising PBS and EDTA.

As used herein, the term "contacting" means treating, immersion, exposing to, rinsing of the biological tissue used in the inventive method.

As used herein, the term "PBS" is directed to a phosphate buffered saline having a pH of 7.4 and containing water based salt solution of disodium hydrogen phosphate, sodium chloride and, in some formulations, potassium chloride and potassium dihydrogen phosphate, PBS is used in biological and medical applications, such as washing cells, transportation of tissues and dilutions, because PBS closely mimics the pH, osmolarity, and ion concentrations of the human body.

The term "aqueous solution" refers to a solution comprising a substance or a compound and water that has been purified to remove contaminants which are able to influence the end product. Preferably, distilled water, double distilled water or deionized water is used in a method of the present invention.

The term "EDTA" is used herein to refer to ethylenediaminetetraacetic acid which is a complexing chelating agent being able to sequester metal ions especially Ike $Fe^{2+}/Fe^{3+}$, $Al^{3+}$, $Mg^{2+}Ca^{2+}$, $Mn^{2+}$, $Zn^{2+}$ and others and to remove them from the solution forming so called EDTA-complexes.

According to embodiment, it is especially important to remove calcium ions from the solution by forming calcium chelator that has been shown to inhibit mineralization of biological tissues, in particular bovine pericardium tissue, It is suggested that EDTA binds to calcium ions on the outer shell of hydroxyapatite crystals which are formed from calcium phosphate crystals thereby chelating and removing calcium ions from the crystals, causing the tissue material to shrink thus deminealizing the material.

Treatment of biological tissues with EDTA hence slows down the progression of calcification by binding calcium before it can react to form hydroxyapatite. Since the calcification of biological tissues used e.g. as bioprosthetic heart valves is a clinically significant problem that contributes to implant failure, it is of significant importance to reduce calcium level in biological tissues used as an implant. Therefore in the present invention, the EDTA treatment can reduce calcium level in biological tissues, especially in bovine or porcine pericardium or a heart valve preferably by 20%, more preferably by 30%, further preferably by 40% and especially preferably by 50%. Further, it is preferable to use EDTA in combination with PBS in order to increase demineralization and compatibility with a human body.

Furthermore, it is preferable to use EDTA, in particular in steps (3) and (4), having a concentration of more than 0.01% by weight, preferably of more than 0.05% by weight, more preferably of more than 0.10% by weight, still preferably of more than 0.15% by weight, and of less than 10.0% by weight, preferably of less than 8.0% by weight, more preferably of less than 6.0% by weight, still preferably of less than 5.0% by weight, further preferably of less than 3.0% by weight. Still further in the present invention, it is preferably to use disodium EDTA.

In a fourth step of the present invention, the bovine pericardium is contacted with a solution comprising glycerol, ethanol and EDTA, and in a fifth step the bovine pericardium is contacted with a glycerol solution in order to further reduce calcification of biological tissue and to dehydrate the bovine pericardium. The following steps describe an iniplernentation of these processes in the method.

After the bovine pericardium has been processed through steps (1) to (3) of the method, they undergo the treatment in a solution comprising glycerol, ethanol and EDTA.

Phospholipids in and around biological tissue cells have been found the most prominent calcification nucleation sites. Therefore, the removal of these tissue components has been proposed to reduce mineralization, in particular calcification. Different studies have shown these to be effective calcification prevention strategies. The organic solvents like ethanol or glycerol or a mixture of ethanol and glycerol can be similarly used for this purpose. For example, the treatment with at least 70% ethanol, preferably with at least 80% ethanol, more preferably with at least 90% ethanol, extracts phospholipids from the tissue while also causing a change in collagen conformation that increases bioprosthesis resistance to collagenase. Thus, ethanol treatment allows extracting almost all phospholipids and cholesterols from the bioprosthesis, thus eliminating calcification of the biological tissue cells. Additionally, ethanol treatment also prevents adsorption of phospholipids and cholesterols from the solution. The method by which glycerol fixes biological tissue is not jet fully understood, but a 98% concentration, preferably 99% concentration, is sufficient to treat the biological tissue to make the tissue more biocompatible and resistant to calcification.

In this respect, it is preferably to treat biological tissue in a solution comprising glycerol, ethanol and EDTA for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm. During this time most of the water molecules presented in biological tissue, in particular pericardial tissue, are replaced with glycerol.

Furthermore, it is preferable to use a mixture of glycerol and ethanol, wherein a volume ratio of glycerol to ethanol is preferably from 1:5 to 5:1, more preferably from 1:4 to 4:1, still preferably from 1:3 to 3:1, further preferably from 1:2 to 2:1.

The bovine pericardium is then removed from the solution and placed in glycerol for further dehydration for at least 60 minutes, preferably for at least 75 minutes, more preferably for at least 90 minutes, at room temperature, in particular at a temperature of 10° C. to 25° C., preferably at a temperature of 15° C. to 25° C., more preferably at a temperature of 18° C. to 22° C., under stirring of not more than 500 rpm, preferably of not more than 300 rpm, more preferably of not more than 50 rpm.

It can further be preferable to use an additional step of contacting or rinsing the bovine pericardium with ethanol having a concentration of at least 70% by volume, preferably with at least 80% by volume, more preferably with at least 90% by volume. The additional step, in particular step (3a), is preferably carried out before contacting the biological tissue with a solution comprising glycerol, ethanol and EDTA. It can further be preferable to carry out another additional step (5a) of contacting the biological tissue with ethanol after the step of contacting the biological tissue with a glycerol and before the step of drying the biological tissue. It can still further be preferable to carry out an additional step (3a) and/or (5a) using a mixture of ethanol and EDTA having a concentration as in step (3) or (4).

The bovine pericardium is removed from the solution and exposed to ambient air or an inert environment, e.g. nitrogen, at room temperature and humidity so as not to adversely affect tissue properties. Preferably, the drying is performed in a dean room at ambient conditions for at least 12 hours, preferably for at least 16 hours, still preferably for at least 20 hours. Further preferably, the drying is performed under high efficiency particulate air (HEPA) filter, in particular under HEPA conditions in a clean room. As used herein, the term "ambient conditions" is directed to the ambient temperature of more than 10° C., preferably of more than 12° C., more preferably of more than 14° C., especially preferably of more than 18° C., and preferably of less than 25° C., more preferably of less than 23° C., further preferably of less than 22° C. Further in the present invention it is preferably to carry out each of steps (1) to (7) at the ambient conditions as described above.

The treated and dried bovine pericardium is then packaged in a container or package essentially free of liquid for subsequent surgical implantation. As used herein, the term "essentially free of liquid" means a non-fluid environment in which the presence of water or other substances is limited to approximately the content of such substances in ambient air.

According to yet another embodiment, in the expanded state, a maximum outer diameter of the proximal section is larger than a maximum outer diameter of the middle section and a maximum outer diameter of the distal section. Such a design has proven to fit best in the pulmonary artery. The larger proximal diameter also ensures that the stent can be fixed at the transition between the pulmonary artery and the right ventricle of the heart, e. the proximal section may even protrude into the ventricle.

In the expanded state, a minimum outer diameter of the stent may further be at the fixture area, wherein the fixture area has an at least substantially cylindrical shape respectively a cylindrical shape over a length of the fixture area along the longitudinal axis, preferably wherein the length of the fixture area is equal to a length of the middle section. The smaller diameter of the stent at the fixture area helps to prevent a compression of the coronary arteries, which wrap around the entire heart.

The skirt may further be arranged to cover the middle section at least from within the middle section, in particular within the fixture area, and parts of the proximal section and optionally parts of the distal section, preferably at most 50% of the distal section, preferably between 20 and 100 ° A of the proximal section and 100% of the middle section. Once in place, the skirt will be pressed against the stent frame due to blood flow through the valve from the proximal to the distal end. Depending on the precise anatomy of the patient, the stents may comprise different sizes and thus also different skirt sizes. For some cases it may better to have a longer skirt, which covers most parts of the stent while in other cases a short skirt, which covers only the middle section and small parts of the proximal section, may be sufficient The ends of the arms at the distal and the proximal ends may lie in a common plane to avoid having single arms that may poke the artery or the ventricle.

The eyelets of the proximal end in particular may projecting beyond the common plane at the ends of the arms. They may especially lie in a further common plane. Such eyelets can help to suture the stent frame to the pulmonary artery.

The ends of the arms of the frame at the proximal and/or the distal end may be arranged coaxially with the longitudinal axis. This allows a better positioning and precision upon deployment of the distal part at the infundibulum, i. a the funnel-shaped part of the pulmonary artery, as well as the valve at the middle part of the pulmonary artery.

According to an embodiment thought lines extending from proximal end to the distal end from the ends of the arms respectively the eyelets taper towards the distal end.

According to a second aspect of the invention a delivery device for delivering a self-expandable stent according to the invention, the delivery device comprising a flush port, a main body part for holding, inflating and/or releasing the stent, and an actuation mechanism for moving the stent to a delivery site.

The device may be preloaded with a stent so that this can be stored ready to use on a shelf in a medical facility to significantly reduce the treatment time of acute aortic syndromes leading to reduced mortality rates of acute aortic syndromes.

The actuation mechanism may have a torque control and may be able to rotate the stent about an axis of the main body. In this way the stent can be positioned in relation to the extremities in an as good as possible manner at the aortic valve, to deploy the valve and stent at the desired delivery site. The device may further be improved with steerable control, to increase precision and accuracy at deployment.

Also, the device may have a knob or the like at the actuation mechanism, with the knob in particular being able to be rotated about an axis of rotation of the actuation mechanism. By turning the knob the lumen is able to deflect and allows a better positioning of the tip and the main body of the delivery device and less stress over the system during deployment. This leads to an improved accuracy of deployment of the delivery device and hence of a stent that is delivered to a delivery site using the delivery device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be described in detail by means of embodiments and with reference to the drawings. These show preferred embodiments. The features described may be configured in various combinations, which are encompassed in this document. The drawings show.

DETAILED DESCRIPTION

Figures 1, 2:
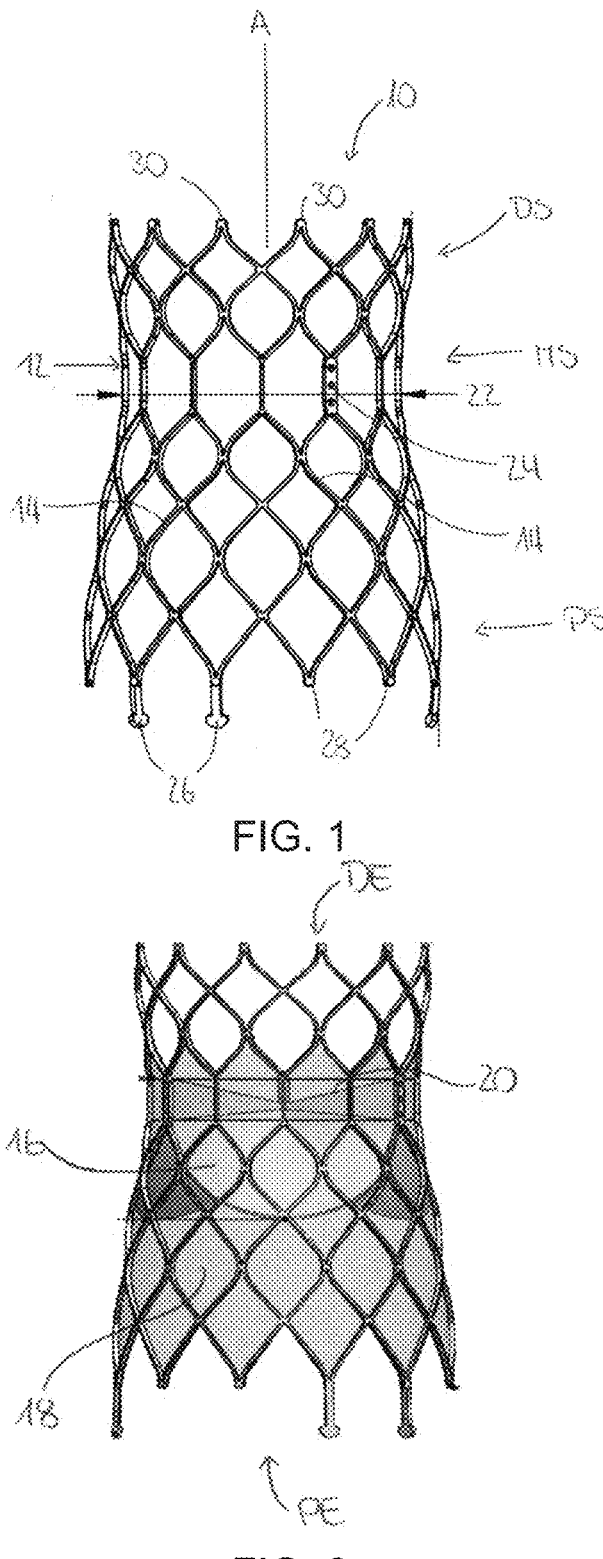
FIG. 1: an exemplary stent frame.
FIG. 2: an exemplary stent frame including a valve and a skirt.

FIG. 1 shows a self-expandable stent 10 configured to be placed in the pulmonary artery of a patient. The stent 10 comprises a frame 12 which is composed of a plurality of arms 14 fabricated of Nitinol. Nitinol is a flexible metal, which comprises the characteristic of being self-expandable. Hence, the stent 10 can be delivered in a compressed state to a point of interest such as the pulmonary artery of a human, where it can self-expand once it is deployed.

The frame 12 further comprises three sections, i.e. a proximal section PS, a middle section MS and a distal section DS, which are all interconnected with each other. The proximal section PS is characterized by comprising the proximal end PE of the stent 10, i. e, said end, which is closer to the heart once the stent is put in place. Consequently, the distal section DS comprises a distal end DE, which is farther away from the heart once the stent is fixed at the pulmonary artery. The middle section MS is arranged between the proximal and the distal section PS, DS.

The middle section MS further includes a valve 16 made out of dry bovine pericardium as well as skirt 18 made out of dry bovine pericardium and polyester (FIG. 2). FIG. 2 also shows the leaflets 20 of the valve 16. The valve 16 can comprise between 2 and 6 leaflets, preferably 3 or 4 leaflets. The characteristics of the skirt 18 will be explained below.

In order to be able to attach the valve 16 to the arms 14, the frame comprises at its middle section a fixation area 22 including several fixation openings 24. Said fixation openings 24 can be used to suture the valve 16 to the respective arms 14. As one can see, the arms 14 at said fixation area 22 are arranged in a parallel manner while at the other sections, e, g, the distal and the proximal section DS, PS, the arms 14 are arranged such that they form a net with diamond-shaped openings. As can be seen, for example, in FIG. 1 the area of the diamond-shaped openings is usually larger when the diameter of the stent 10 is bigger.

In the example shown in FIG. 1, one arm 14 comprises three openings 24 at which the valve 16 can be fixed. It may also be possible that every arm 14 or every second arm 14 or maybe only as many arms 14 as leaflets 20 comprise a fixation area 22 with respective fixation openings 24. In another example (not shown) it may also be possible that the fixation openings 24 are arranged at a bridge, connecting two adjacent arms 14 at the fixation area 22 such that the fixation openings 24 are arranged between two adjacent arms 14.

Due to anatomical reasons of the pulmonary artery and the right ventricle of a heart,the skirt 18 of the stent 10 does not only surround the valve 16 at the fixation area 22 but also up to 100% of the proximal section PS (see FIG. 2) or at least parts of the proximal section PS (see FIG. 3) to prevent leakage between the stent 10 and the ventricle of the patient's heart. Furthermore, the skirt 18 can also cover parts of the distal section DS, which can be seen in FIGS. 2 and 3. Thus, the skirt 18 can cover up to 50% of the distal section DS, between 20 and 100% of the proximal section PS and 100% of the middle section MS.

Figure 3:
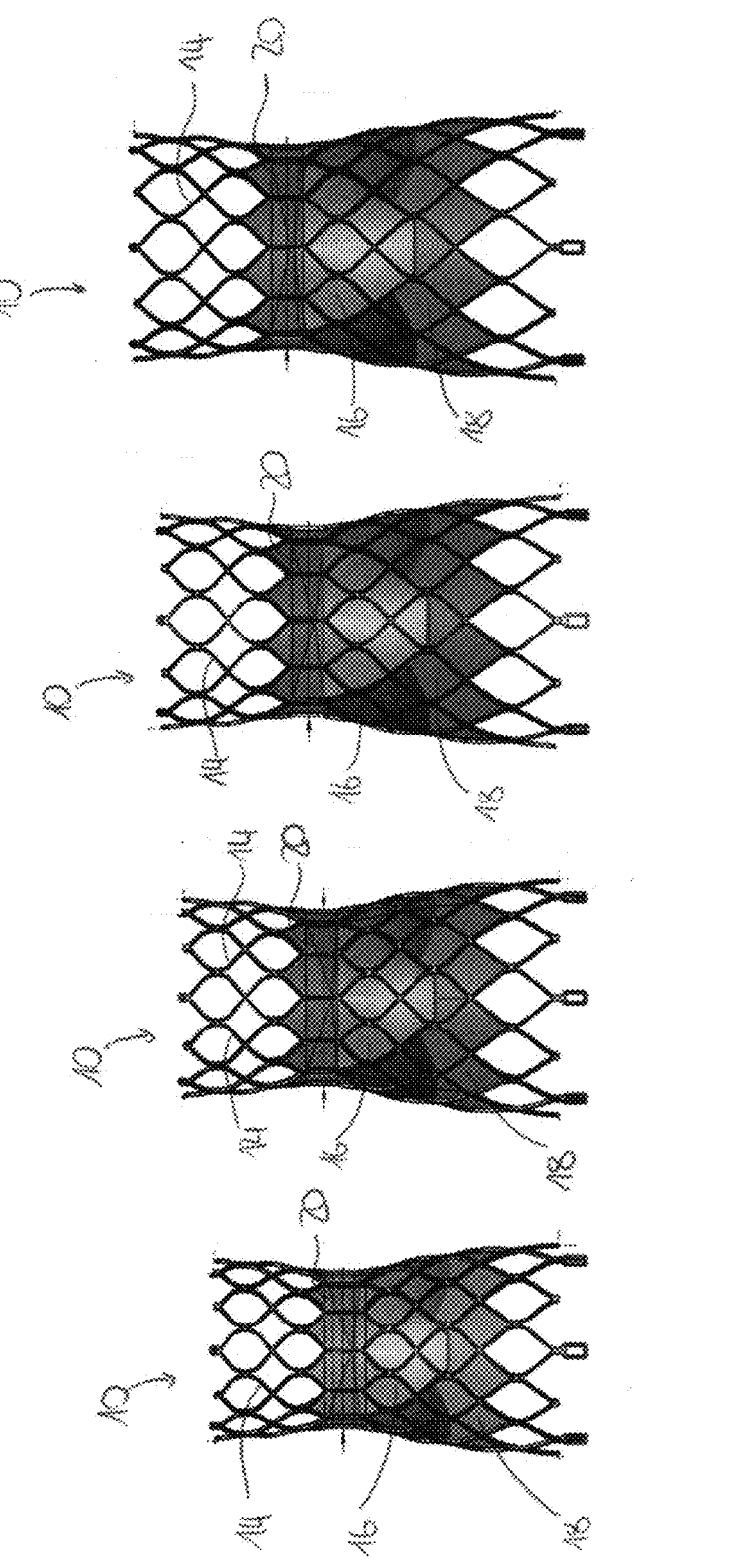
FIG. 3: different stents of different sizes.

In order to being able to attach the stent 10 at its respective point of interest, i. e. the pulmonary artery, the stent 10 comprises eyelets 26 at its respective proximal and/or distal end PE, DE (see e. g. FIG. 3). That is, after being expanded, the stent 10 does not only hold itself in place by fitting into the pulmonary artery but also by being sutured. This way, it may also be possible to attach the proximal end PE of the stent 10 at the transition of the pulmonary artery and the right ventricle of a heart or at the wall of the right ventricle itself such that the stent 10 protrudes inside the ventricle. The exact attachment point and technique can thus be chosen according to the different conditions at the different hearts which are being treated with the invention.

As one can see especially in FIGS. 1 to 3, the stent 10 comprises different diameters at its different sections. The middle section MS which comprises at least the fixation area 22 comprises the smallest diameter. This way, a compression of the coronary arteries, which wrap the whole heart, can be prevented.

The diameters of the proximal and the distal ends PE, DE are therefore larger. It may be possible that said two diameters are of the same size. In most embodiments it has shown that it can be advantageous to choose the diameters such that the proximal end PE comprises a larger diameter than the distal end DE such that lines, which connect the ends 28 of the arms 14 of the proximal end PE with the ends 30 of the arms at the distal end DE taper. The reason for this is that at the proximal end PE the stent 10 can protrude inside the ventricle of the heart. Therefore the diameter of said end needs to large enough such that it can be sutured to the hearts wall or at least seals the transition between the ventricle and the pulmonary artery sufficiently.

The ends 28, 30 of the arms 14 at both ends of the stent 10 can lie in a common plane. Furthermore, the ends 28, 30 of the arms 14 of the frame 12 at the proximal and the distal end PE, DE are arranged coaxially with the longitudinal axis A of the frame 12, The eyelets 26, which are used to suture the stent 10 to the artery project beyond said plane (see esp. at the proximal end PE in FIG. 3). Said eyelets 26 can comprise a rectangular outer shape with a rectangular opening for suturing the stent 10 to the pulmonary artery. Generally, those eyelets 26 can also comprise a different shape, e. g. a circular shape, for both the outer and the inner shape.

Figure 7:
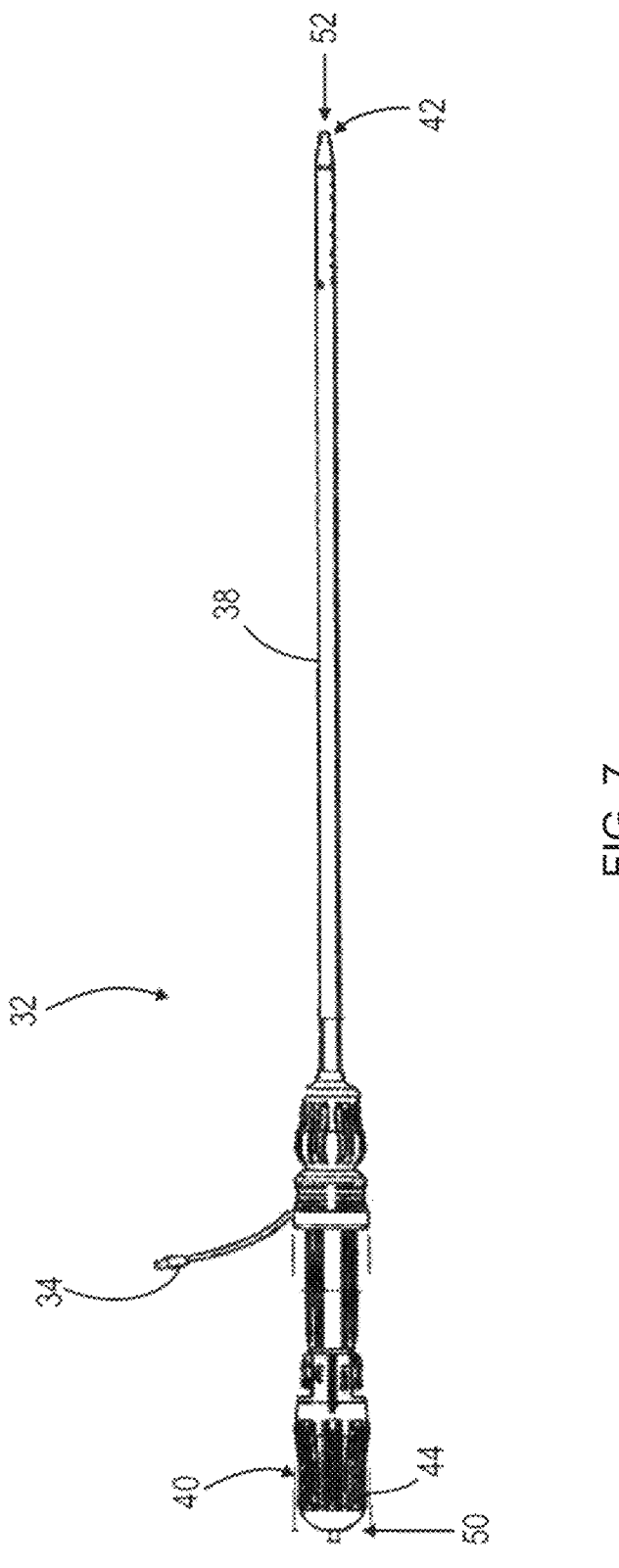
FIG. 7: a delivery device for delivering a self-expandable stent.

Fig. 7 shows a delivery device 32 for the self-expandable stent 10 also known as a catheter. The delivery device 32 comprises a flush port 34 for flushing internal cavities of the delivery device (not shown) and a main body 36 for holding, inflating and/or releasing the stent 10. The device may further comprise two valved introducers (not shown) to allow access to the stent 10. Initially two diagnostic catheters (not shown) can be introduced via said two valved introducers together with the preloaded stent for delivering the stent to the target delivery site, i.e. the patients' heart.

The delivery device 32 further includes an actuation mechanism 40 for moving the stent 10 to a delivery site.

The main body 36 is arranged at an inner shaft at an end of the lumen 38 that extends between the actuation mechanism 40 and a tip 42 of the catheter. The stent 10 can thus be guided to the delivery site by means of the actuation mechanism 40 that has a torque control and can rotate the stent 10 about an axis A of the frame 12. The (longitudinal) axis A extends between the proximal and the distal end PE, DE of the frame 12 of the stent 10.

The actuation mechanism 40 comprises a knob 44 at a distal end 50 of the actuation mechanism 40. On turning the knob 44 about an axis B of the actuation mechanism 40 which extends between the distal end 50 and a proximal end 52 of the actuation mechanism 40, the lumen 38 is able to deflect. This enables the tip 42 of the lumen 38 to occupy various positions (not shown). Such a deflection of the lumen 38 reduces the overall stress in the system which leads to a better positioning of the stent 10 at a delivery site and an overall improved accuracy of deployment of the delivery device 32 and hence of a stent 10 that is delivered to a delivery site using the delivery device 32.

On delivering the stent 10 to the delivery site, i.e. the heart, by means of the delivery device 32, the arterial femoral access is preferably used. The lumen 38 is then moved through the arteries to the heart.

The position of the stent 10, the diagnostic catheters and/or of the delivery device 30 may be tracked using e.g. x-rays in order to monitor radiopaque markings present at the stent 10 and/or the delivery device 30. Thereby the precision and accuracy during deployment of the stent 10 within the heart can be further increased, so that the replacement valve 16 can be positioned accurately at the aortic valve.

Figure 4:
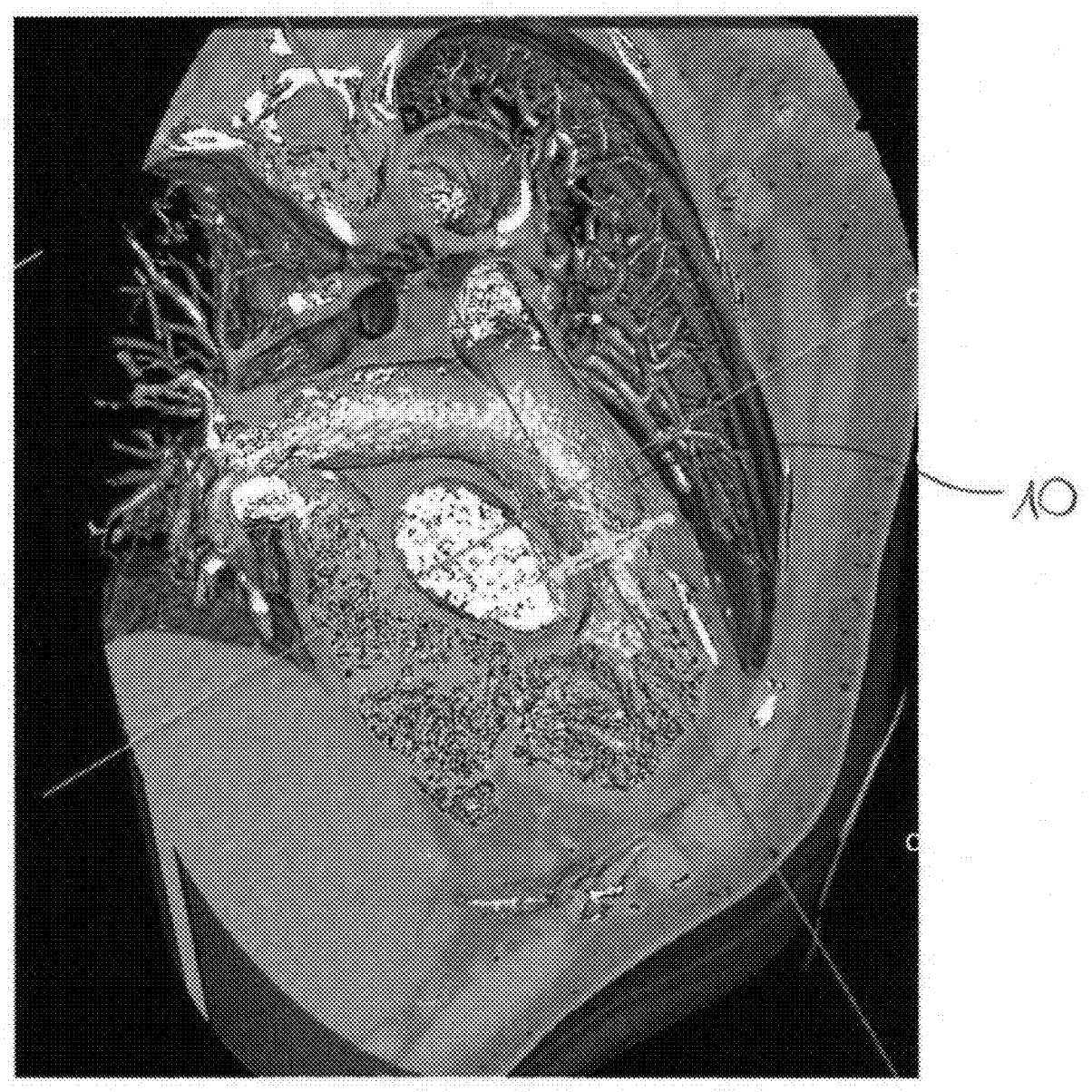
FIG. 4: a CT reconstruction picture of a stent according to the invention inserted in a patient's artery.
Figure 5:
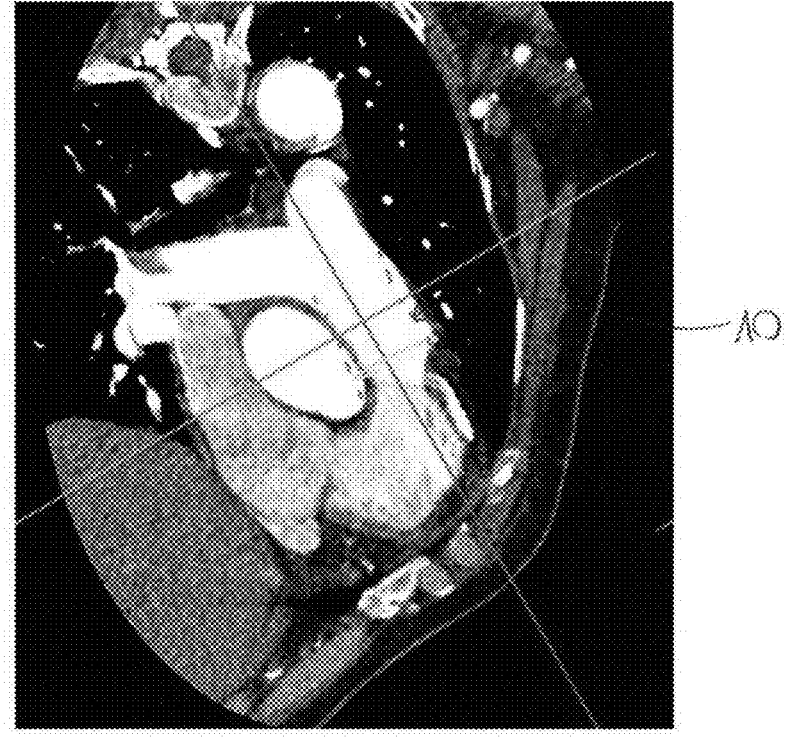
FIG. 5: the CT reconstruction picture of FIG. 4 at a different angle.
Figure 6:
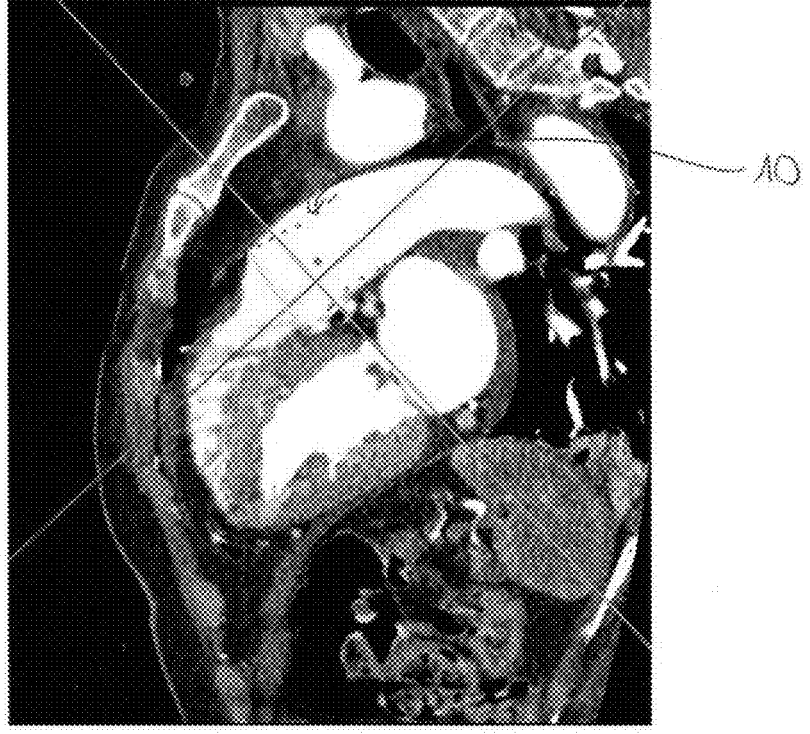
FIG. 6: the CT reconstruction picture of FIGS. 4 and 5 at another angle.

In FIGS. 4 to 6 one can see different MRI pictures of a stent 10, which has been deployed at the pulmonary artery of a patient, preferably by a delivery device 32 according to the invention. The different pictures in FIGS. 4 to 6 show the same stent 10 from different angles. As one can see in those MRI pictures, the stent 10 is in the expanded state and has been deployed at the transition between the pulmonary artery and the right ventricle of the patient.

What is claimed is:

1. A self-expandable stent with a proximal section, a middle section and a distal section arranged at a longitudinal axis of the stent, the stent having a dry valve made of bovine pericardium with a calcium content selected in a range of 0.01 to 0.1 g/Kg arranged at the middle section thereof, wherein the dry valve is rehydrated with a saline solution upon placement at a point of interest with a catheter, a skirt surrounding the dry valve at least at the middle section, the skirt comprising at least one of bovine pericardium and polyester, wherein the stent further comprises eyelets arranged at at least one of a distal end of the distal section and a proximal end of the proximal section for fixing the stent at an artery, and wherein the stent comprises a frame composed of a plurality of arms forming the proximal section, the middle section and the distal section with the sections being interconnected, and the stent comprising a fixture area at the middle section of the frame with the arms being arranged in parallel to each other at the fixture area and the middle section comprising one or more fixture openings at said fixture area for fixing the valve at the frame, with said fixture openings being present in the arms or respectively between the arms which are directly connected to one another.

2. The self-expandable stent according to claim 1, wherein the middle section comprises a length which is approximately 5 to 30% of a total length of the stent.

3. The self-expandable stent according to claim 1, wherein one or more such openings are provided in one or more arms of the middle section.

4. The self-expandable stent according to claim 1, wherein two or more such openings are provided in one or more arms of the middle section.

5. The self-expandable stent according to claim 1, wherein the dry bovine pericardium has a maximum tensile stress selected in a range of 20 to 25 MPa.

6. The self-expandable stent according to claim 1, wherein the bovine pericardium has a tensile stress selected in a range of 12 to 15 MPa after rehydration.

7. The self-expandable stent according to claim 1, wherein the dry valve comprises between two and six leaflets.

8. The self-expandable stent according to claim 1, wherein the dry valve comprises three or four leaflets.

9. The self-expandable stent according to claim 1, wherein the dry bovine pericardium is formed by using a method of treatment comprising the following steps:

soaking of the bovine pericardium treated with a cross-linking agent with a saline solution;

contacting the soaked bovine pericardium with an aqueous solution comprising Hydrogen Peroxide;

contacting the bovine pericardium with an aqueous solution comprising PBS and EDTA;

contacting the bovine pericardium with a solution comprising glycerol, ethanol and EDTA; and contacting the bovine pericardium with a glycerol solution.

10. The self-expandable stent according to claim 1, wherein, in an expanded state, a maximum outer diameter of the proximal section is larger than a maximum outer diameter of the middle section and a maximum outer diameter of the distal section.

11. The self-expandable stent according to claim 1, wherein, in an expanded state, a minimum outer diameter of the stent is present at the fixture area, wherein the fixture area has an at least substantially cylindrical shape respectively a cylindrical shape over a length of the fixture area along the longitudinal axis.

12. The self-expandable stent according to claim 11, wherein the length of the fixture area is equal to a length of the middle section.

13. The self-expandable stent according to claim 1, wherein the skirt is arranged to cover the middle section at least from within the middle section, and parts of the proximal section and optionally parts of the distal section.

14. The self-expandable stent according to claim 13, wherein the skirt is arranged to cover the middle section within the fixture area.

15. The self-expandable stent according to claim 13, wherein the skirt is arranged to cover at most 50% of the distal section and 100% of the middle section.

16. The self-expandable stent according to claim 15, wherein the skirt is arranged to cover between 20% and 100% of the proximal section.

17. The self-expandable stent according to claim 1, wherein all of the ends of the arms at the distal and the proximal ends lie in a common plane.

18. The self-expandable stent according to claim 17, with the eyelets of the proximal end projecting beyond the common plane at the ends of the arms.

19. The self-expandable stent according to claim 18, wherein the eyelets lie in a further common plane.

20. The self-expandable stent according to claim 1, wherein the ends of the arms of the frame at the proximal and/or the distal end are arranged coaxially with the longitudinal axis.

21. The self-expandable stent according to claim 1, wherein lines extending from proximal end to the distal end from the ends of the arms respectively the eyelets taper towards the distal end.

22. A delivery device for delivering a self-expandable stent:

the self-expandable stent comprising:

a proximal section, a middle section and a distal section arranged at a longitudinal axis of the stent, the stent having a dry valve made of bovine pericardium with a calcium content selected in a range of 0.01 to 0.1 g/Kg arranged at the middle section thereof, wherein the dry valve is rehydrated with a saline solution upon placement at a point of interest with the delivery device, a skirt surrounding the dry valve at least at the middle section, the skirt comprising at least one of bovine pericardium and polyester, wherein the stent further comprises eyelets arranged at at least one of a distal end of the distal section and a proximal end of the proximal section for fixing the stent at an artery, and wherein the stent comprises a frame composed of a plurality of arms forming the proximal section, the middle section and the distal section with the sections being interconnected, and the stent comprising a fixture area at the middle section of the frame with the arms being arranged in parallel to each other at the fixture area and the middle section comprising one or more fixture openings at said fixture area for fixing the valve at the frame, with said fixture openings being present in the arms or respectively between the arms which are directly connected to one another; and the delivery device comprising:

a flush port;

a main body part for holding, inflating and/or releasing the stent; and an actuation mechanism for moving the stent to a delivery site, wherein the actuation mechanism has a torque control and can rotate the stent about an axis of the main body; and the delivery device having a knob at the actuation mechanism, with the knob in particular being able to be rotated about an axis of rotation of the actuation mechanism.

* * * * *